United States Patent [19]

Takahashi et al.

[11] Patent Number: 4,557,755

[45] Date of Patent: * Dec. 10, 1985

[54] MICROENCAPSULATED AGRICULTURAL CHEMICAL AND PROCESS OF PREPARATION THEREOF

[75] Inventors: Masaaki Takahashi, Tokyo; Yuji Hattori; Yuriko Igarashi, both of Iwaki, all of Japan

[73] Assignee: Kureha Kagaku Kogyo Kabushiki Kaisha, Nihonbashi, Japan

[ * ] Notice: The portion of the term of this patent subsequent to Jul. 17, 2001 has been disclaimed.

[21] Appl. No.: 401,241

[22] Filed: Jul. 23, 1982

[30] Foreign Application Priority Data

Jan. 18, 1982 [JP] Japan .................................. 57-6350

[51] Int. Cl.$^4$ ...................... A01N 37/00; A01N 37/18; A01N 25/28; B01J 13/02
[52] U.S. Cl. ........................................ 71/100; 71/118; 264/4.7; 424/19; 424/32; 427/213.34; 428/402.21; 428/402.24; 514/936
[58] Field of Search ..................... 264/4.7; 427/213.34; 428/402.21, 402.24; 424/19, 32; 71/100, 118

[56] References Cited

U.S. PATENT DOCUMENTS

| | | | |
|---|---|---|---|
| 3,074,845 | 1/1963 | GEary | 424/32 X |
| 3,516,941 | 6/1970 | Matson | 252/182 X |
| 3,607,775 | 9/1971 | Yoshida et al. | 252/631 |
| 3,778,383 | 12/1973 | Schibler et al. | 252/316 |
| 4,105,823 | 8/1978 | Hasler et al. | 264/4.7 X |
| 4,223,060 | 9/1980 | Raine et al. | 428/341 X |
| 4,460,722 | 7/1984 | Igarashi et al. | 427/213.34 X |

FOREIGN PATENT DOCUMENTS

| | | |
|---|---|---|
| 0046415 | 2/1982 | European Pat. Off. . |
| 1444414 | 3/1962 | Fed. Rep. of Germany . |
| 2147237 | 9/1971 | Fed. Rep. of Germany . |
| 1507739 | 4/1978 | United Kingdom . |
| 2094257 | 9/1982 | United Kingdom . |

*Primary Examiner*—Richard D. Lovering
*Attorney, Agent, or Firm*—Wegner & Bretschneider

[57] ABSTRACT

A microencapsulated agricultural chemical comprises an agricultural chemical as an active ingredient having a solubility of not more than 1 g in 100 ml of water at 20° C. and vapor pressure of not more than 760 mmHg at 60° C. and a microcapsule wall enclosing the agricultural chemical therein and the microcapsule wall comprises a water-soluble cationic urea resin and at least one of prepolymer composed of formaldehyde and at least one compound selected from the group consisting of urea, melamine and thiourea. The microcapsule is prepared by dispersing the agricultural chemical in an aqueous medium containing the water-soluble cationic urea resin, an anionic surfactant and at least one of the prepolymer and maintaining pH of the obtained dispersion within an acidic range to polycondense the water-soluble cationic urea resin and at least one of the prepolymers.

10 Claims, 5 Drawing Figures

MICROENCAPSULATED AGRICULTURAL CHEMICAL AND PROCESS OF PREPARATION THEREOF

The present invention relates to a microencapsulated agricultural chemical and a process for preparing the same.

Agricultural chemicals are generally required distinguished effect in the practical usage without exerting undesirable influences on environment. However, there are cases where an agricultural chemical used actually in the field cannot exhibit the expected effects such as effective pest control and a high yield of crops due to the rapid decomposition of the agricultural chemical by sunlight, moisture and rain water. These facts depend on the practical instability of the agricultural chemical itself in the field even if the agricultural chemical is strong enough to exhibit its effectiveness in a laboratory. In such cases, the factors concerning the decomposition of the agricultural chemical are its stability and resistance to light and water. Furthermore, in consideration of the possible environmental pollution, the undesirable influences to organisms other than the target to be controlled, for instance, the scattering of the applied agricultural chemicals outside of the area to be applied by air drifting in the case of aerial application, should be rigorously prevented.

In order that an agricultural chemical can exhibit the expected effect and in order to avoid its undesirable influences on animals and plants other than the target, the improvement of the techniques of formulation of agricultural chemicals is useful and important. For instance, the development of the powdery preparation for use in flooded rice fields has improved the efficiency of application of agricultural chemicals, and the development of the granular preparation has introduced the "hand scattering" into the operation of application of agricultural chemicals, improved the persistency of agricultural chemicals due to the slow-release of the active ingredient from the granular preparation and broadened the appropriate season for application of agricultural chemicals. Furthermore, the development of the minute granular preparation comprising particles of size between those of powder and granule has reduced the undesirable scattering of minute powdery particles of the agricultural chemical outside of the field to be treated with the application, which is one of the factors resulting in environmental pollution. Thus, the development of formulation techniques of agricultural chemicals has raised the effect of agricultural chemicals placed in a more preferable state of formulation.

As one of the new formulation techniques which is expected to manufacture a preparation exhibiting a more preferable performance, microencapsulation of agricultural chemicals has attracted the attention of the persons concerned in the art.

Namely, by introducing the technique of microencapsulation into the formulation of agricultural chemicals, it becomes possible to produce a preparation releasing slowly an agricultural chemical enclosed therein and to protect the agricultural chemical from the main factors of decomposition thereof, such as sunlight and/or moisture. Further, effective utilization of agricultural chemicals and energy-saving in agricultural operation are expected by the microencapsulation.

Microencapsulation of agricultural chemicals has been widely studied hitherto, and a number of proposals have been suggested; however, in view of microencapsulation from the above-mentioned sense, satisfactorily microencapsulated agricultural chemical has not yet appeared.

From viewpoint of the material for the microcapsule wall, a number of methods for formulation of a microencapsulated agricultural chemical have been proposed while utilizing, for instance, gelatine (refer to, for instance, Japanese Patent Laying-Open No. 99969/75), polyamide, polyurea, polyurethane and polyester (refer to U.S. Pat. No. 4309213), polyvinyl acetate and polyvinyl ether (refer to FR-A No. 2430259), polyurethane-polyurea (refer to U.S. Pat. No. 4230809), polyamide-polyurea (refer to Japanese Patent Laying-Open No. 4643/73), and the like.

However, in the microcapsule prepared while using gelatine, its wall becomes much too dense to allow the release of the content of the capsule to outside through the wall membrane when the microcapsules are dried, and conversely, when the microcapsules are wet, the wall membrane becomes swollen to allow the release of the content within a short time period, resulting in the poor control of the persistency of the effect of the agricultural chemical. The last-mentioned defect still remains in the specified capsule which has a more compact wall membrane made of a water-soluble polymeric material such as gelatine brought into reaction with an aminoplast-resin prepolymer or the like (refer to Japanese Patent Laying-Open No. 38097/77).

Microcapsules with their wall membrane comprising polyurea, polyamide, polyurethane and the like are produced by a surface polymerization technique, and in this case, it is necessary that one of the monomers for the material of wall membrane is soluble into the agricultural chemical to be enclosed in the microcapsule, and accordingly, such a method can not be applied to the agricultural chemical which is not soluble into the monomer. In addition, even in the case where the agricultural chemical is soluble in the monomer, there is a demerit due to the remaining effect of unreacted monomer as well as the reduction of the effect of agricultural chemical in the case where the agricultural chemical reacts with the monomer.

As still another method of microencapsulation, a method utilizing only a polycondensate of urea-formaldehyde (refer to Japanese Patent Publication No. 30282/71) and a method disclosed in U.S. Pat. No. 3,778,383 can be mentioned. According to the last-mentioned method, after dispersing the substance to be encapsulated into a medium of dispersion in the presence of a reactive tenside, the tenside is converted irreversibly into an insoluble state to prepare a primary suspension of capsules, and then a solution of aminoplast precondensate is mixed with the primary suspension to convert the aminoplast precondensate into an insoluble state, thus preparing a secondary suspension of capsules. However, in the method according to the procedures for making wall membrane of capsules while utilizing aminoplast precondensate, agglutination of the thus-formed microcapsules cannot be avoided and accordingly, the product contains inevitably the agglomerated particles resulting in the difficulty of controlling the releasing rate of the agricultural chemical as the core substance to outside of the microcapsules and of obtaining the microcapsules in a powdery state.

One of the large and important objects expected to the microencapsulation of agricultural chemicals is the effective use of the agricultural chemical and the other is the energy-saving in agricultural operations. In order to attain the objects, it is required that the microencapsulated agricultural chemical is released in line with the object of using the agricultural chemical while the agricultural chemical is remaining within the microcapsule in a stable state during the predetermined time period after being applied. In spite of the many proposals on the method for microencapsulating of agricultural chemicals, few of them have been put into practical use. From view point of the material for wall membrane of the microcapsule, only few of microcapsules of agricultural chemical has been practiced while having gelatine membrane or polyamide membrane containing respectively a specified agricultural chemical with the extremely restricted method of application in the field. In short, such microencapsulated agricultural chemicals have not yet fully answered to the expectation of introducing microencapsulating technique into agricultural chemicals.

There are the facts that (1) each proposed method itself has its own demerit mentioned above, (2) it is very difficult to adjust the rate of release of the agricultural chemical from the microcapsule to outside corresponding to the optional object of using the agricultural chemical and (3) the thus-prepared microcapsule is not sufficiently resistant to water, weather and sunlight for carrying out the release of the agricultural chemical in the crop field effectively.

It is an object of the invention to provide a microencapsulated agricultural chemical which is excellent in moisture stability and light stability and may have a desired time and rate of release of the enclosed active ingredient. Another object of the invention is to provide a process for microencapsulation of an agricultural chemical.

The microencapsulated agricultural chemical of the invention comprises an agricultural chemical as an active ingredient having a solubility of not more than 1 g in 100 ml of water at 20° C. and a vapor pressure of not more than 760 mmHg at 60° C. (hereinafter referred to as core substance) and a microcapsule wall enclosing the core substance therein which is a polycondensate of a water-soluble cationic urea resin with at least one of prepolymer made of formaldehyde and at least one compound selected from the group consisting of urea, melamine and thiourea.

The microencapsulation process of the invention comprises dispersing a core substance in an aqueous medium containing a water-soluble cationic area resin, an anionic surfactant and at least one of the prepolymer and maintaining pH of the obtained dispersion within an acidic range.

BRIEF DESCRIPTION OF THE DRAWINGS

Of the annexed drawings.

The diameter of the microencapsulated agricultural chemical of the invention can be optionally selected from the range of 1 to 100 microns, and the thickness of microcapsule wall can be freely selected from the range of 0.02 to 10 microns. The freely selected thickness of microcapsule wall is not expectable in the microcapsule prepared by the surface polymerization technique.

Furthermore, according to the invention, it is possible to select the rate of release of the core substance from the microcapsule freely within a certain range while maintaining the thickness of the microcapsule wall at a predetermined level by adjusting the proportion of formaldehyde occupying the material of the microcapsule wall. Consequently, according to the invention, it is possible to prepare the microencapsulated agricultural chemical with an optional rate of release of the core substance even in the case where the wall membrane is extremely thin. In addition, even in the case where the very thick wall is necessary for maintaining the mechanical strength thereof, the rate of release of the core substance can be kept at a necessary level.

Furthermore, the microcapsule wall of the microencapsulated agricultural chemical of the invention is excellent in resistance to water and sunlight, for instance, it can keep the microencapsulated agricultural chemical in a stable state during a long period of 2 to 3 months after applying to the crop field. Conversely, the wall material of the microcapsule can be decomposed gradually in soil into inorganic substances by soilborne fungi.

The core substance capable of being microencapsulated according to the invention includes a pesticide, a fungicide, a biocide, a herbicide, an anti-viral agent, an attractant and repellant and may be in an optional physical state of liquid or solid. Concrete example of the core substance of the invention is a pesticide such as phenitrothion, diazinon, chlorobenzilate, O,O-di-n-propyl 4-methylthiophenyl phosphate, disulfoton, pyrethrins and synthetic pyrethroids, a fungicide such as probenazole, isoprothiolane, S-benzyl diisopropyl phosphorothiolate and edifenphos, a herbicide such as butachlor, oxadiazon and bentazone, an attractant such as 9-dodecen-1-al and 8-dodecen-1-yl acetate, a repellant such as nor-farnesene and $\beta$-farnesene and a biocide such as isothiazolone derivative.

On microencapsulating such a core substance, each substance is usually subjected to microencapsulation; however, when the core substances are chemically stable to each other on coexistence, more than two substances may be simultaneously microencapsulated. In addition, the core substance may be microencapsulated after diluting with an inert and water-insoluble solvent. In the case of a solid core substance, it may be microencapsulated at room temperature or higher temperature after dispersing directly the solid substance in a liquid medium or after dissolving the solid core substance into a hydrophobic solvent and further dispersing the thus-prepared solution in a liquid medium as minute droplets.

The microencapsulated agricultural chemical enclosing the core substance may be prepared as follows.

In the case where the core substance to be microencapsulated is in a liquid state, for instance, the method for preparing a microcapsule for pressure-sensitive recording paper disclosed in European Patent Publication No. 0046415-A1 can be applied. Namely, the microcapsule wall is prepared by dispersing the core substance or the solution thereof in an aqueous mixture containing the prepolymer, the water-soluble cationic urea resin and the anionic surfactant and adding an acid catalyst to the thus-formed dispersion to polycondense the prepolymer and the water-soluble cationic urea resin. By this procedure, the anionic surfactant and the water-soluble cationic urea resin concentrate onto the interface between water and the particles or droplets of the core substance by electrostatic force to stabilize the emulsion and simultaneously cause complex-coacervation in the aqueous phase, and the coacervations accumulate gradually on the particles or droplets of the core substance to enable the formulation of a compact wall membrane of the microcapsules.

On the other hand, in the case where the core substance is solid at an ordinary temperature, the microencapsulation can be carried out by the dispersion of the substance.

In addition, when the surface of the core substance is negatively charged, the amount of the anionic surfactant can be reduced, and in the case where spherically shaped microcapsules are desired, the microencapsulation may be carried out after emulsifying the solid core substance at a temperature of higher than the melting point thereof or after dissolving the solid core substance in a hydrophobic solvent.

Furthermore, it is preferable to modify the method for microencapsulation in order to obtain the microencapsulated agricultural chemicals having a preferable rate of release in accordance with the mode of application of the microencapsulated agricultural chemical. For instance, in the case where the product is used as a fumigant or used after mixing into granular soil particles for culture, it is required that the wall membrane of the microencapsulated agricultural chemical is fairly tough and not easily release the core substance during storage. In such cases, it is necessary that the weight ratio of the material for wall membrane to the core substance is raised and the wall membrane is more compact than in other cases. For obtaining such a product, the conditions of the polycondensation should be set up fairly mild, for instance, a reaction temperature as low as possible and accordingly for a long period of reaction time. The microcapsules prepared under the conditions are obtained as a slurry or a free-flowing powder after drying as it is, with its core substance completely protected from its release during storage.

On the other hand, in the case where the microencapsulated agricultural chemical is used in aerial application, the release of the core substance must begin from the time of application, and for that purpose, better permeability of the core substance through the wall membrane is required. In such a case, the extent of the release of the core substance can be controlled by reducing the molar ratio of formaldehyde in the raw material of prepolymer to urea, thiourea, melamine or the mixture of more than two of them and raising the reaction rate of polycondensation to reduce the compactness of the wall membrane. The desired rate of release is also available by adequately intermixing several kinds of microcapsules with the respective rates of release mutually different.

In the invention, the very important characteristics are that the water-soluble cationic urea resin and the anionic surfactant which have the opposite charges to one another are used together with the prepolymer. A more stable dispersion of the core substance may be obtained due to the presence of a small amount of the water-soluble cationic urea resin and the anionic surfactant, therefore, a uniform and compact wall can be obtained.

The microencapsulating process of the invention is described in detail hereinafter.

In the first step of the process of the invention, the core substance is dispersed in an aqueous mixture, in which a water-soluble cationic urea resin and an anionic surfactant are present, by a suitable means such as homogenizer, stirrer or ultra-sonic so that an appropriate diameter of the liquid droplet or the particle of the core substance is obtained. The prepolymer may be added preliminarily to the aqueous mixture before dispersion, however, it may be added to the aqueous mixture during or after the dispersion process. Then an acid-catalyst is added to the aqueous dispersion containing the prepolymer with gentle stirring. The pH and the temperature are maintained in the range of 2.5° to 6.0° and 15° to 60° C., respectively, for 2 to 50 hours, and a slurry of microcapsules is obtained. In addition, an adequate amount of water may be added during the polycondensation reaction.

It is preferable to neutralize the obtained slurry of microencapsulated agricultural chemicals in advance of the application thereof.

The prepolymer used in the invention includes a urea-formaldehyde prepolymer (hereinafter referred to as UF prepolymer), a melamine-formaldehyde prepolymer (MF prepolymer), a thiourea-formaldehyde prepolymer (TUF prepolymer), a melamine-urea-formaldehyde prepolymer (MUF prepolymer), a melamine-thiourea-formaldehyde prepolymer (MTUF prepolymer), a urea-thiourea-formaldehyde prepolymer (UTUF prepolymer) and a melamine-urea-thiourea-formaldehyde prepolymer (MUTUF prepolymer).

MF prepolymer herein indicates any one of methylol melamines such as mono- to hexamethylol melamine, a mixture of the methylol melamines of different hydroxymethylation, a mixture of the methylol melamine(s), melamine and formaldehyde and any oligomer(s) obtained by the further reaction of melamine and formaldehyde, e.g. methylol melamine(s) with the polymerization degree of 2 to 10 which may be subjected to microencapsulation in the form of a transparent colloidal solution obtained by treating the oligomers with hydrochloric acid. The MF prepolymer may be easily prepared by heating a mixture of melamine and formaldehyde under alkaline conditions, and thus obtained aqueous reaction mixture may be subjected to a microencapsulation process.

UF prepolymer of the invention indicates any one of methylol ureas such as mono- to tetramethylol urea, a mixture of the methylol ureas of different degree of hydroxymethylation, a mixture of the methylol urea(s), urea and formaldehyde, and any oligomer(s) obtained by the further reaction of urea and formaldehyde, e.g.

methylol urea(s) with the polymerization degree of 2 to 5 and having hydrophilic group(s), which may be used in the form of a transparent colloidal solution.

TUF prepolymer in the invention indicates any one of methylol thiourea such as mono- to tetramethylol thiourea, a mixture of the methylol thioureas of different degree of hydroxymethylation, a mixture of the methylol thiourea(s), thiourea and formaldehyde, and any oligomer(s) obtained by the further reaction of thiourea and formaldehyde, e.g. methylol thiourea(s) with the polymerization degree of 2 to 5 and having hydrophilic group(s) which may be used in the form of a transparent colloidal solution.

On the other hand, MUF prepolymer, MTUF prepolymer, UTUF prepolymer and MUTUF prepolymer obtained by heating under alkaline condition formaldehyde and at least two compounds of melamine, urea and thiourea may be used in the invention singly or in a mixture of at least two of them or in a mixture with MF prepolymer TUF prepolymer and/or UF prepolymer.

In preparing the prepolymer, the molar ratio of formaldehyde to melamine, urea or thiourea gives a very important influence on the formation of the wall membrane of the microcapsule, and the molar ratio of formaldehyde to melamine is 1.0 to 9.0, preferably, 1.6 to 7.0; the molar ratio of formaldehyde to urea is 0.6 to 4.0, preferably, 0.8 to 3.0 and the molar ratio of formaldehyde to thiourea is 0.6 to 4.0, preferably 0.8 to 3.0.

On the other hand, the ratio of melamine:urea:thiourea affects the physical properties of the wall membrane of the microcapsule, and accordingly, the ratio is selected to obtain the microcapsule with the strength and the permeability to the core substance in accordance with the object of use of the microcapsules. The amount of the prepolymer used in microencapsulation according to the invention is preferably 0.03 to 1.0 g/g of the core substance.

The water-soluble cationic urea resin of the invention indicates a urea-formaldehyde resin prepared by introduction of a cationic modifier. The water-soluble cationic urea resin is easily prepared by adding a modifier to a urea-formaldehyde prepolymer and then polycondensing in a known manner. A modifier includes tetra ethylene pentamine, diaminoethanol, dicyandiamide, diethyl aminoethanol, guanyl-urea and the like.

The weight ratio of the water-soluble cationic urea resin to the prepolymer is preferably in the range of 0.01 to 2.0.

The anionic surfactant of the invention includes salts of aliphatic acids, sulfate esters of higher alcohols, salts of alkylarylsulfonates and the like, preferably sodium dodecylbenzenesulfonate.

The weight ratio of the anionic surfactant is in the range of 0.01 to 0.1 parts by weight to one part of the water-soluble cationic urea resin, and this weight ratio causes a stable dispersion in the wide pH range, i.e. 2.5 to 6.0.

The acid-catalyst includes a low molecular weight carboxylic acid such as formic acid, acetic acid and citric acid, an inorganic acid such as hydrochloric acid, nitric acid and phosphoric acid, an acidic salt or an easily hydrolyzable salt such as aluminum sulfate, titanium oxychloride, magnesium chloride, ammonium chloride, ammonium nitrate, ammonium sulfate and ammonium acetate and a mixture thereof.

According to the method of the invention, it is possible to microencapsulate an agricultural chemical in any shape or form which has hitherto been difficult to microencapsulate by any one of the known methods, and in the same time, the method of the invention has a distinguishing feature of being capable of freely controlling the thickness and the permeability to the core material of the wall membrane of the microcapsule.

The invention will be explained concretely while referring to the following non-limiting examples.

EXAMPLE 1

1-1. Preparation of prepolymer

An aqueous solution of a melamine-formaldehyde prepolymer (hereinafter referred to as M4F prepolymer, M4F meaning that the molar ratio of formaldehyde to melamine is 4:1) was prepared by mixing 63 g of melamine and 162 g of aqueous 37% by weight solution of formaldehyde (hereinafter referred to as formalin) adjusted to pH of 9.0 with the addition of aqueous 2% by weight solution of sodium hydroxide, reacting melamine and formaldehyde at 70° C. and adding 225 g of water just after the dissolution of melamine into the aqueous phase followed by stirring for 3 min.

Separately, an aqueous solution of a urea-formaldehyde prepolymer (hereinafter referred to as U 1.8 F prepolymer, U 1.8 F meaning that the molar ratio of formaldehyde to urea is 1.8) was prepared by mixing 60 g of urea and 146 g of formalin adjusted to pH of 8.5 with the addition of triethanolamine and reacting urea and formaldehyde at 70° C. for one hour.

1-2. Preparation of a water-soluble cationic urea resin

Sixty grams of urea and 162 g of formalin were mixed with stirring, and after adjusting pH of the mixture to 8.8 with the addition of triethanolamine, the mixture was brought into reaction at 70° C. for 30 min. Into 40 g of the thus obtained reaction mixture, 24 g of water and 6 g of tetraethylenepentamine were added, and while stirring the mixture at 70° C., its pH was adjusted to 3 by the addition of aqueous 15 % solution of hydrochloric acid and it was left to react for one hour. Then, the reduced pH of the reaction mixture with the progress of the reaction was re-adjusted again to 3 with the addition of aqueous 10% by weight solution of sodium hydroxide, and the reaction was allowed to continue at 55° C. until the viscosity of the reaction mixture became 200 c.p. At this time point, the reaction mixture was neutralized by the addition of aqueous 10% by weight of sodium hydroxide, and 400 g of water was added to the reaction mixture to obtain an aqueous solution of a water-soluble cationic urea resin.

1-3. Microencapsulation

A mixture of 13.6 g of the M4F prepolymer, 6.8 g of the U 1.8 F prepolymer, 158 g of the aqueous solution of the cationic urea resin prepared above, 62 g of water and 1 g of triethanolamine was adjusted to pH of 5.2 by adding aqueous 10% by weight solution of citric acid, and then 3 g of aqueous 10% by weight solution of sodium alkylbenzenesulfonate(Neopelex ®, manufactured by Kao-Atlas Co., Japan) was added to the mixture.

After adding 150 g of diazinon into the thus-prepared solution, the mixture was subjected to homogenization in a homogenizer to be an emulsion of droplets having average diameter of 2 to 8 microns, and then the emulsion was gently stirred while maintaining the temperature thereof at 30° C. and adjusting the pH therof to 3.6 by addition of aqueous 10% by weight solution of citric acid. After one hour 200 g of water was added to the mixture, and after one another hour pH of the mixture was adjusted to 2.8 followed by stirring for 2 hours. Then the temperature of the mixture was raised to 40° C., and the mixture was further stirred for 3 hours to complete the microencapsulation. The content of the active ingredient in the microencapsulated diazinon of the invention was 95% by weight.

EXAMPLE 2

Microencapsulation of diazinon was carried out in the same manner as in Example 1 except for using 41 g of the M4F prepolymer and 20.5 g of the U 1.8 F prepolymer. The content of diazinon in the microencapsulated agricultural chemical of the invention was 85% by weight.

EXAMPLE 3

After adjusting pH of the mixture of 20 g of a water-soluble cationic urea resin (Uramin ® P-1500, manufactured by Mitsui-Toatsu Co., Japan), 82.4 g of the M4F prepolymer prepared in Example 1, 150 g of water and 1 g of triethanolamine to 5.0 with the addition of aqueous 10% by weight solution of citric acid, 3 g of aqueous 10% by weight solution of Neopelex ® (refer to Example 1) was added to the mixture.

After adding 150 g of fenitrothion further to the above-mentioned mixture, the whole system was subjected to homogenization in a homogenizer to be an emulsion containing droplets of 5 to 10 microns in average diameter, and while maintaining the temperature of the emulsion at 40° C. it was gently stirred and the pH was adjusted to 3.8 with the addition of aqueous 10% by weight solution of citric acid. Then, after one hour, aqueous 10% by weight solution of citric acid was added again to the whole mixture to adjust the pH thereof to 3.0 and 100 g of water was added, and further by stirring the whole system as it was for 15 hours the microencapsulation was completed. The content of fenitrothion in the microencapsulated agricultural chemical was 87.4% by weight.

EXAMPLE 4

After adjusting the pH of a mixture of 25 g of Uramin ® P 1500 (refer to Example 3), 54.2 g of the U 1.8 F prepolymer prepared in Example 1, 180 g of water and 1.0 g of triethanolamine with the addition of aqueous 10% by weight solution of citric acid to 5.5, 3.7 g of aqueous 10% by weight solution of Neopelex ® (refer to Example 1) and 200 g of fenitrothion were added, and the whole system was subjected to homogenization in a homogenizer until the average diameter of emulsified droplets became 5 to 10 microns. While gently stirring the emulsion and maintaining the emulsion at a temperature of 35° C., aqueous 10% by weight solution of citric acid was added to the emulsion to bring its pH to 3.8. After one hour of reaction, 150 g of water was added to the acidic emulsion and it was stirred for 2 hours. Then after adjusting pH to 3.0 with aqueous 10% solution of citric acid and one hour reaction, 150 g of water was again added and it was stirred for 15 hours to complete the microencapsulation. The amount of fenitrothion in the thus obtained microencapsulated agricultural chemical was 86.9% by weight.

EXAMPLE 5

Into a mixture of 25 g of Uramin ® P-1500 (refer to Example 3) and 200 g of water, which was adjusted to pH of 5.0, 2.5 ml of an aqueous solution of Neopelex ® (refer to Example 1) was added, and further 150 g of probenazole was added while stirring the mixture well. Then, while gently stirring the mixture at 40° C., 80 g of the M4F prepolymer (refer to Example 1) and 40 g of the U 1.8 F prepolymer (refer also to the Example 1) were added to the mixture, and the thus prepared whole mixture was adjusted to pH of 3.6 with the addition of aqueous 10% by weight of citric acid solution. After 2 hours, the mixture was again adjusted to pH of 3.0 with the addition of aqueous 10% by weight solution of citric acid to continue the reaction for one hour. Then, 10 ml of aqueous 10% by weight solution of resorcinol and 180 g of water were added to the mixture, and the mixture was left for 15 hours at 30° C. for maturation of wall membrane of microcapsules to obtain a slurry of microencapsulated probenazole. The content of probenazole in the microcapsule was 71% by weight.

EXAMPLE 6

During the same operation as in Example 5, just after adding 180 g of water into the mixture thus prepared, 40 g of U 1.8 F prepolymer (refer to Example 1) was again added to the mixture and stirring was continued. After one hour of the stirring, the mixture was adjusted to pH of 3.0 by adding aqueous 10% solution of citric acid and then after adding 5 ml of aqueous 10% solution of resorcinol, the reaction was continued for 30 min. 40 g of the U 1.8 F prepolymer was then added to the mixture and the mixture was stirred for one hour. Then, the mixture was adjusted to pH of 3.0 with the addition of aqueous 10% solution of citric acid and 5 ml of aqueous 10% by weight solution of resorcinol was further added to continue the reaction for 30 min. Thereafter, the temperature of the whole system was reduced to 30° C. to mature the product for 15 hours. Thus, the slurry of microencapsulated probenazole was obtained. The content of probenazole in the microcapsule was 41.5% by weight.

The respective two slurries of microencapsulated probenazole obtained in Examples 5 and 6 were filtered and washed, and the thus recovered wet microcapsules were dried to be the free-flowing powdery products of microcapsules.

EXAMPLE 7

A mixture of 28.0 g of melamine, 29.1 g of urea, 34.6 g of thiourea and 209.3 g of formalin adjusted to pH of 9.0 by aqueous 5% by weight solution of sodium hydroxide was brought into reaction at 70° C. for 30 min to obtain an aqueous solution of a MUTUF prepolymer.

Eighty grams of the aqueous solution of the MUTUF prepolymer prepared above, 316 g of the aqueous solution of the water-soluble cationic urea resin prepared in Example 1, 2 g of triethanolamine and 124 g of water were mixed together, and after adjusting pH of the mixture to 5.2 with the addition of aqueous 25% by weight solution of citric acid, 6 ml of aqueous 10% solution of ammonium lauryl sulfate (Emal ® AD-25, manufactured by Kao-Atlas Co., Japan) was added to the mixture.

Into the thus prepared mixture, 300 g of ethyl N,N-di-n-propyl thiocarbamate(so-called EPTC in Japan) was added, and the whole system was subjected to homogenization in a homogenizer to be an emulsion containing droplets of EPTC having an average diameter of 3 to 15 microns. After adjusting pH of the emulsion to 3.6 with the addition of aqueous 25% by weight solution of citric acid while gently stirring at 30° C., the emulsion was brought into reaction for 2 hours. Then the pH of the whole system was reduced to 3.0 and the reaction was continued for 3 hours, and 200 g of water was added to the whole system. After warming the whole system to 45° C., it was brought into reaction for one hour to complete the microencapsulation. The content of EPTC of the microcapsule was 86% by weight.

EXAMPLE 8

Twenty-eight grams of melamine, 29.1 g of urea, 34.6 g of thiourea and 209.3 g of formaline adjusted to pH of 9.0 by an aqueous 5% solution of sodium hydroxide were mixed and reacted at 70° C. for 30 min to obtain an aqueous solution of melamine-urea-thiourea-formaldehyde prepolymer.

Eighty grams of the aqueous solution of the prepolymer, 316 g of the aqueous solution of the water-soluble cationic urea resin prepared in Example 1, 2 g of triethanolamine and 124 g of water were mixed and adjusted to pH of 5.2 by an aqueous 25% solution of citric acid. Into the mixture was added 6 ml of an aqueous 10% solution of ammonium lauryl sulfate (Emal ® AD-25, manufactured by Kao-Atlas Co., Japan).

Into the mixture, 300 g of butachlor was homogenized to an emulsion containing droplets with average diameter of 3 to 15 microns. The emulsion was adjusted to pH of 3.6 by an aqueous 25% solution of citric acid at 30° C. while stirring gently and the reaction proceeded for further 2 hours. After adjusting pH of the reaction mixture to 3.0 by an aqueous 25% solution of citric acid and reacting for further 3 hours, 200 g of water was added. The temperature of the reaction mixture was raised up to 45° C. and the reaction proceeded for one hour to complete microencapsulation. The content of butachlor in the microcapsule was 86%.

EXAMPLE 9

After adjusting a mixture of 20 g of Uramin ® P 1500, 150 g of water and 1 g of triethanolamine to pH of 5.2 by the addition of an aqueous 10% by weight solution of citric acid, 3.5 g of an aqueous 10% by weight solution of Neopelex ® was added to the mixture to prepare Aqueous solution A.

A solution (hereinafter referred to Mixed Solution B) obtained by adding 10 g of nor-farnesene (a 3:1 molar mixture of trans- to cis isomers) which is an alarm pheromone against into 90 g of 1-cumyl-2-phenylethane was mixed with Aqueous solution A, and the thus prepared mixture was subjected to homogenization for 20 min to be a dispersion containing particles of 5 micrometers in average diameter. After 5 min gentle stirring of the dispersion at 30° C., 100 g of the M4F prepolymer prepared in Example 1 and 50 g of the U 1.8 F prepolymer also prepared in Example 1 were added to the dispersion, and the mixture was adjusted to pH of 4.0 by the addition of an aqueous 10% by weight solution of citric acid. After 4 hours of the pH-adjustment, 200 g of water was added to the mixture and after adjusting the mixture to pH of 3.0 by the addition of an aqueous 10% by weight solution of citric acid, stirring of the mixture was continued for 10 hours, and then the mixture was adjusted to pH of 7.0 by the addition of an aqueous 25% by weight solution of ammonia. The concentration of Mixed Solution B in the thus prepared slurry-like dispersion of microencapsulated of Mixed Solution B was 15% by weight.

EXAMPLE 10

Into a mixture of 20 g of Uramin ® P-1500 (refer to Example 3) and 200 g of water, which was adjusted to pH of 5.0, 3.0 ml of an aqueous solution of Neopelex ® (refer to Example 1) was added, and further 100 g of allethrin was added while stirring the mixture well. Then, while gently stirring the mixture at 30° C., 112 g of the M4F prepolymer (refer to Example 1) and 56 g of the U 1.8 F prepolymer (refer also to the Example 1) were added to the mixture, and the thus prepared whole mixture was adjusted to pH of 3.6 with the addition of aqueous 10% by weight solution of citric acid. After 2 hours, the mixture was again adjusted to pH of 3.0 with the addition of aqueous 10% by weight solution of citric acid to continue the reaction for one hour. Then, 180 g of water were added to the mixture, and the mixture was left for 15 hours at 40° C. for maturation of wall membrane of microcapsules to obtain a slurry of microencapsulated allethrin. The content of probenazole in the microcapsule was 62% by weight.

COMPARATIVE EXAMPLE 1

Microencapsulation of diazinon was carried out according to nearly the same procedures as those disclosed in Japanese Patent Laying-Open No. 7313/71 as follows.

In the first place, a reactive tenside was prepared as follows.

Into 590 parts by weight of aqueous 36.5% by weight solution of formaldehyde containing methanol, 126 parts by weight of melamine was dissolved at 60° C. while adding 18 parts by weight of aqueous 25% by weight solution of ammonia. From the thus prepared solution, 132 parts by weight of a mixture of water and methanol was distilled off under a reduced pressure for about 20 min while heating the solution at 80° C. To the distillation residue, 490 parts by weight of n-butanol was added, and the mixture was subjected to vacuum distillation to collect the distillate, which was separated into water and n-butanol. The thus collected n-butanol was returned to the reactor, and on the other hand, the aqueous layer amounting to 118 parts by weight was separated from the content of the reactor. To the aqueous layer, 3 parts by weight of aqueous 85% by weight solution of formic acid dissolved in 5 parts by weight of n-butanol was added to the aqueous layer, and the thus prepared mixture was subjected to distillation to distill n-butanol amounting to 452 parts by weight in total. As a distillation residue, 552 parts by weight of a viscous solid resin was obtained.

On heating 532 parts by weight of the thus obtained resin of melamine/n-butanol (containing one mol of melamine) together with 104 parts by weight of triethanolamine while stirring at 120° C. for 1.5 hours and further heating at 135° to 140° C. for 1.5 hours, 76 parts of n-butanol was distilled from the mixture. After cooling the residue, 560 parts by weight of a viscous and transparent product which dissolves easily into aqueous 10% by weight solution of acetic acid was obtained. The product, so-called reactive tenside, contained 78% by weight of solid component.

In the second place, diazinon was microencapsulated while using the reactive tenside as follows.

Into a solution of 20.0 g of the reactive tenside dissolved in a mixture of 98.0 g of water and 2.0 g of glacial acetic acid, 200 g of diazinon was added, and the mixture was emulsified in a homogenizer. After adjusting the emulsion with 400 ml of water and 6 ml of aqueous 85% by weight solution of phosphoric acid to pH of 2.1, the average diameter of the droplet in the emulsion was 2 to 8 microns.

On leaving the emulsion to stand still for 3 hours at room temperature and further 2 hours at 60° C., diazinon appeared on the surface of the emulsion, and the viscosity of the system has a risen.

After adjusting the pH of the emulsion to 6.0 with an addition of aqueous 24% by weight solution of ammonia, 30.1 g of an aminoplast-precondensate prepared by mixing 10.2 g of melamine and 19.9 g of aqueous 37% by weight solution of formaldehyde at 60° C. for 30 min was added to the emulsion together with 43 g of water under agitation which was continued further for 30 min. Then, 3.2 ml of aqueous 85% by weight solution of phosphoric acid was added to the emulsion, and after heating the emulsion to 40° C., it was stirred for 30 min. After stirring the emulsion further one hour at 60° C., the microencapsulation was completed by cooling the emulsion to 20° C. and adjusting its pH to 9.0 with the addition of aqueous 24% by weight solution of ammonia. The content of diazinon in the microcapsule was 83% by weight.

COMPARATIVE EXAMPLE 2

A mixture of 20 parts by weight of allethrin and 30 parts by weight of aqueous 10% by weight solution of gelatine was subjected to homogenization to obtain an emulsion of droplets of 2 to 8 microns in diameter, and while gently stirring and heating the emulsion to 50° C., 40 parts by weight of aqueous 4% by weight solution of carboxymethylcellulose and 50 parts by weight of water were added to the emulsion, and then the pH of the emulsion was adjusted to 4.4 with an addition of aqueous 5% by weight solution of acetic acid.

After 10 min of the adjustment of pH, the emulsion was cooled to 5° C. and 4 parts by weight of aqueous 25% by weight solution of glutaraldehyde was added to the cooled emulsion. After one hour of the addition of the aldehyde, the pH of the mixture was raised to 10 by the addition of aqueous 10% by weight solution of sodium hydroxide and the mixture was re-heated to 50° C. under agitation for additional 30 min. On cooling the emulsion to room temperature, a slurry of microcapsules with wall membrane made of gelatine was obtained. The amount of diazinon in the microcapsule was 85% by weight.

COMPARATIVE EXAMPLE 3

A mixture of 10 parts by weight of allethrin and 43.4 parts by weight of aqueous 10% by weight solution of gelatine was subjected to homogenization to obtain an emulsion of droplets of 2 to 8 microns in average diameter, and while gently stirring and heating the emulsion to 50° C., 58 parts by weight of aqueous 4% by weight solution of carboxymethylcellulose and 73 parts by weight of water were added to the emulsion, and then the pH of the emulsion was adjusted to 4.4 with an addition of aqueous 5% by weight solution of acetic acid.

After 10 min of the adjustment of pH, the emulsion was cooled to 5° C. and 5.8 parts by weight of aqueous 25% by weight solution of glutaraldehyde was added to the cooled emulsion. After one hour of the addition of the aldehyde, the pH of the mixture was raised to 10 by the addition of aqueous 10% by weight solution of sodium hydroxide and the mixture was re-heated to 50° C. under agitation for additional 30 min. On cooling the emulsion to room temperature, a slurry of microcapsules with wall membrane made of gelatine was obtained. The amount of allethrin in the microcapsule was 61% by weight.

EXAMPLE 11

Test for elution of active ingredient from microcapsule to water

In order to examine the extent of elution of the agricultural chemical (active ingredient) from the microcapsule to water, the following test was carried out while using the microcapsule specimens different in the amount of wall membrane such as those of Examples 1 and 2 and the microcapsule with wall membrane made of gelatine of Comparative Example 2 for comparison. The test was carried out as follows.

Figure 1:
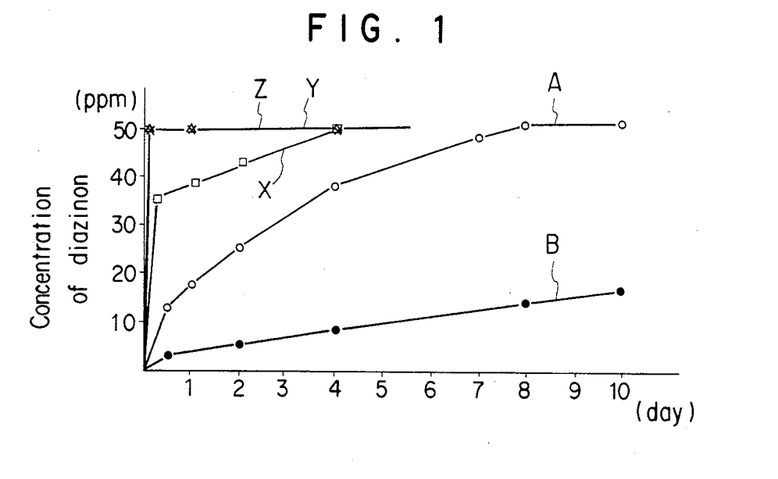
FIG. 1 shows the rate of elution of an active ingredient, diazinon, from the microencapsulated diazinon of the invention (Examples 1 and 2) as compared to those from a comparative product (Comparative Examples 1 and 2) and from a commercial formulation.

An amount of the respective microencapsulated diazinon, corresponding to 50 mg of the active ingredient (diazinon) was put into a 200 ml conical flask, and after adding 100 ml of water into the flask, it was closely stoppered and shaken in an incubator at 30° C. and at 130 reciprocations/min. An aliquot was taken from the aqueous phase in the flask at intervals as the time passed by, and the thus obtained specimens of the aqueous phase were subjected to extraction with n-hexane, the extract having been analyzed for diazinon by the ordinary method of gaschromatography. The amount of diazinon in the extract was converted to the concentration of diazinon in the aqueous phase of the flask to show the exudation of diazinon as the time passed by. The results are shown in FIG. 1 while taking the concentration of diazinon in the aqueous phase in the ordinate and taking the time in days in the abscissa. In FIG. 1, A, B, X, Y and Z respectively concern those data of microcapsules in Example 1, Example 2, Comparative Example 1, Comparative Example 2 and a commercial wettable powder of diazinon.

For reference, the concentration of diazinon in saturation in water at 20° C. is 40 ppm.

As are seen in FIG. 1, the concentration of diazinon exuded from the microencapsulated diazinon in gelatine membrane reached to saturation after only 2 hours of shaking in water as in the case of the commercial wettable powder. On the other hand, the microcapsule according to the invention is very stable even in water and is capable of slowly releasing the active ingredient, and moreover, by changing the amount of wall membrane of the capsule it is possible to change the rate of release.

EXAMPLE 12

Effects of ultraviolet rays on the microcapsule

Effects of ultraviolet ray on the microencapsulated agricultural chemical were examined by using the microencapsulated agricultural chemicals respectively having nearly the same amount of wall membrane but different materials for wall membrane, i.e., those of Example 10, Comparative Example 3 and neat allethrin.

Each of the microencapsulated agricultural chemicals, in this case, allethrin was put into two Petri dish of 9.0 cm in diameter and 2 cm in height in an amount corresponding to 300 mg of the encapsulated allethrin, and one of the dish was placed in a cabinet at 30° C. and exposed to ultraviolet rays from an ultraviolet lamp (FL-20S-BL-NL, made by Toshiba Electric Works, Japan, with wave length ranging 3290 to 4000 Å, centered at 3600 Å) installed just above the dish at a distance of 20 cm for 24 hours, and the residual amount of allethrin in the microcapsule was determined. The results of test are shown in Table 1.

TABLE 1

| Specimen | Initial content of active ingredient (% by wt.) | Loss % of active ingredient only due to ultraviolet rays |
| --- | --- | --- |
| Example 10 | 62 | 20.6 |
| Comparative Example 3 | 61 | 49.7 |
| Neat allethrin | — | 48.6 |

As are seen in Table 1, the loss due to ultraviolet rays was smaller in the microencapsulated allethrin according to the invention than in Comparative Example 3 and neat allethrin.

EXAMPLE 13

Preliminary test on persistency of the product

Figure 2:
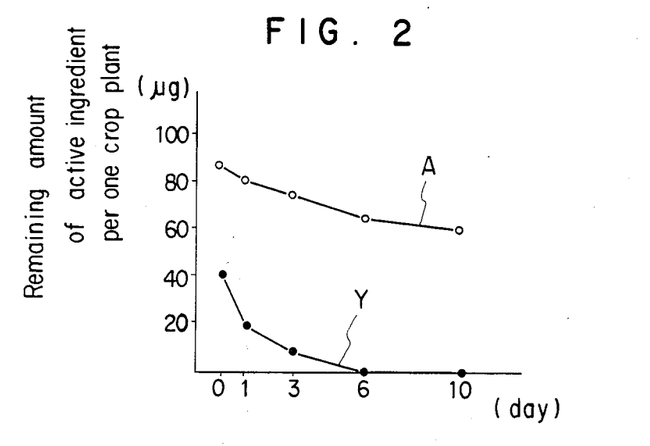
FIG. 2 shows the remaining amount of an active ingredient, diazinon, adhered to the crop plants after applying the microencapsulated diazinon of the invention (Example 1) as compared to that of a commercial formulation.

After 10 days of transplanting the young seedlings of rice plant grown in a box for 20 days after germination into pots of 9 cm in diameter at a rate of 5 seedlings/pot, each of the microencapsulated diazinon prepared in Example 1 containing 95% by weight of diazinon and the commercialized wettable powder containing 34% by weight of diazinon was dispersed in water to correspond to a concentration of 500 ppm of the active ingredient, diazinon, and the aqueous dispersion was sprayed under a pressure of 2 kg/cm$^2$ and at a volume rate of 150 ml/m$^2$ of the surface area of the pot onto the seedlings. Then, the amount of diazinon in and on the seedlings was determined periodically as the time passed by. The results are shown in FIG. 2 wherein the residual amount of diazinon on one seedling was taken in the ordinate and the time in days after application was taken in the abscissa, Curve A showing the result of the microcapsules of Example 1 and Curve Y showing that of the commercialized wettable powder.

EXAMPLE 14

Test for the persistency of pesticidal activity

Figure 3:
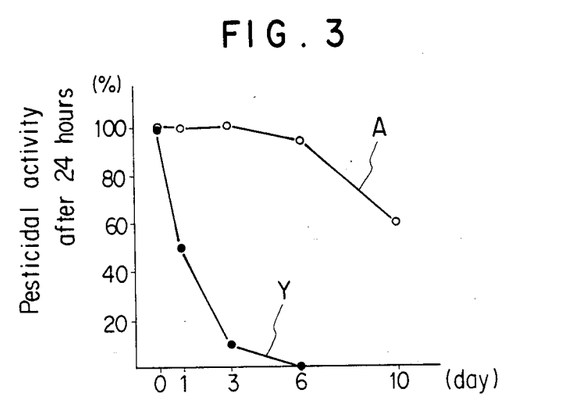
FIG. 3 shows the persistency of the pesticidal activity after applying the microencapsulated diazinon of the invention (Example 1) as compared to that of a commercial formulation.

Onto the rice seedlings transplanted and applied with the microencapsulated diazinon of Example 1 or the commercialized wettable powder of diazinon in a similar manner to that in Example 13, female adults of *Nephotettix cincticeps* were put onto the seedlings repeatedly at a rate of 10 insects/pot on the day of application and after 1, 3, 6 and 10 days of the application, and the mortality of the insect during one hour after putting was observed. The results are shown in FIG. 3 wherein the mortality of the insect was taken in the ordinate and the days after application were taken in the abscissa, Curve A showing the results of the microencapsulated diazinon of Example 1, and Curve Y showing the results of the wettable powder.

From the results of Examples 13 and 14, it was found that the product of the invention showed an adhered amount of diazinon onto the rice seedlings as large as 2 times of that in the case of the wettable powder, and the pesticidal activity remains far longer in the case of the product of the invention than in the case of the wettable powder.

EXAMPLE 15

Figure 4:
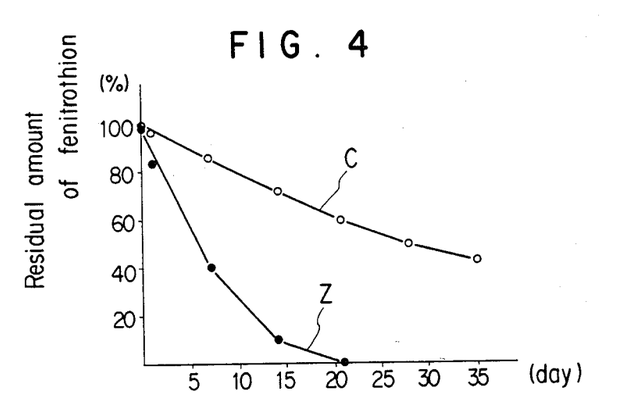
FIG. 4 shows the residual amount (%) of the core substance, fenitrothion, enclosed in the microencapsulated fenitrothion of the invention (Example 3) as the time passes after applying the microencapsulated fenitrothion in the field as compared to that of a commercial formulation.
Figure 5:
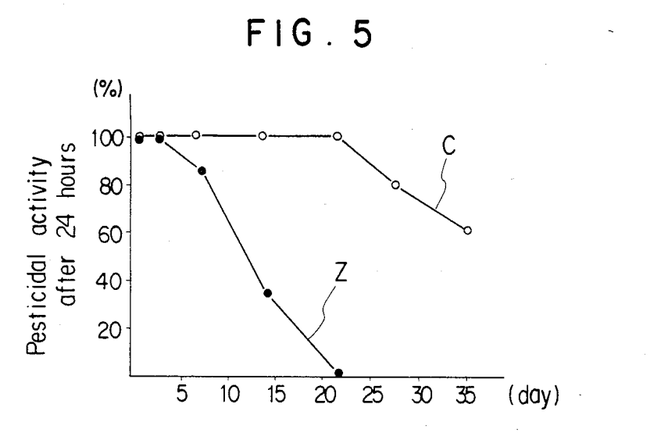
FIG. 5 shows the persistency of the pesticidal activity after applying the microencapsulated fenitrothion of the invention (Example 3) as compared to that of a commercial formulation.

Test for the persistency of pesticidal activity and of the agricultural chemical itself Each of the microencapsulated fenitrothion prepared in Example 3 containing 87.4% by weight of fenitrothion and a commercialized wettable powder containing 40% by weight of fenitrothion was diluted with water to be an aqueous dispersion containing 2500 ppm of fenitrothion, and each aqueous dispersion was placed on a sheet of filter paper of diameter of 9 cm in Petri dishes of 9 cm in diameter and 2 cm in height at 0.32 ml (corresponding to 0.8 mg of fenitrothion)/dish. After placing the Petri dishes in a room heated by steam heater to 25° C., the residual amount of fenitrothion in the dish was determined periodically as the time passes by, and in the same time, male adult *Musca domestica* was put into the dish repeatedly two times at the time point of determination of the residual amount of fenitrothion to see the mortality within 24 hours of the putting, the number of the insect being 20/dish. The results are shown in FIGS. 4 and 5, wherein Curves C show the results of the microencapsulated fenitrothion according to Example 3 of the invention and Curves Z show those of the wettable powder.

EXAMPLE 16

Two specimens of the microencapsulated agricultural chemicals according to the invention, namely, that prepared in Example 5 containing 71% by weight of probenazole and that prepared in Example 6 containing 41.5% by weight of probenazole were tested on their influences on the rice plant growing in seedling boxes, and on their activities of controlling a plant disease inoculated on the rice seedlings grown of the seedling boxes while comparing to the influences and the activity of pest control carried out by a commercialized granular formulation containing 8% by weight of probenazole as follows:

In each of the three seedling boxes, a well blended mixture of 3 kg of dried and sifted soil from a paddy field and an amount of each of the test specimens corresponding to 2 g of probenazole was introduced, and after sowing a predetermined amount of rice seeds and moisturing the soil in the box, the boxes were kept in a green house at 25°±2° C. and 70% RH for 20 days to assess the germination and the growth of rice plants.

After observing and recording the growth of the rice seedlings, the seedlings were transplanted to the soil in pots of 9 cm in diameter with their adhered soil at a rate of 3 seedlings per pot, and grown in the same green house for 20 days.

Then, an aqueous dispersion of spores of *Pyricularia oryzae* taken from the diseased rice plants was sprayed onto the seedlings to inoculate them, and the disease spots appearing on the leaves of the seedling were counted after 7 days of inoculation to find the rate of controlling according to the following formula for calculation:

$$\text{Rate of controlling} = \frac{C - T}{C} \times 100$$

wherein C is the average number of disease spots on control and T is the average number of disease spots on the treated seedlings, the control having been grown in the soil without containing any chemicals other than ordinary fertilizers, and given a treatment of application of 25 g of the commercialized granular formulation containing 8% by weight of probenazole on the day of transplantation from the seedling box to the pot, 5 hours in advance of the transplantation.

The results of the test are shown in Table 2.

As are seen in Table 2, the influence of the microencapsulated agricultural chemical according to the invention on the germination of seeds and the growth of the germinated seedlings of *Oryza sativa* was almost unobservable, and particularly in the case of the microencapsulated probenazole of Example 6 having a larger amount of wall membrane, the growth of the seedlings was better than the control seedlings grown in the soil without addition of any chemicals other than fertilizers. On the other hand, the seedlings which had germinated and have grown in the soil mixed with the commercialized granular formulation containing 8% by weight of probenazole were too poor to be transplanted to the pots.

Fairly desirable control against *Pyricularia oryzae* could be effected on the seedlings which had germinated and have grown in the soil containing the microencapsulated agricultural chemical according to the invention to the same extent as in the seedlings which had germinated in the soil without containing any chemicals other than fertilizer and have been treated with the commercial granular formulation containing 8% by weight of probenazol before 5 hours of transplantation.

seed potatoes has been planted at the same rate of 40 g of the thiocarbamate per are of the field, and the state of growth of weeds in the field was observed time by time until the harvest.

As the results, the time period during which the growth of weeds in the field was effectively suppressed was longer in the field where the microcapsule of the invention had been applied than in the field where the commercial herbicidal formulation had been applied with a statistically larger crop in the former.

EXAMPLE 18

A mixture of 2 g of the microcapsule slurry containing 0.03 g of alarm pheromone prepared in Example 9 and 1 g of an aqueous 10% by weight solution of polyvinyl alcohol was spread uniformly on sheets of filter paper of 7.5 cm in length and 3 cm in width, and the sheets loaded with the microencapsulated alarm pheromone were placed in a dish of 10 cm in diameter to be dried naturally.

Separately, 0.03 g of nor-farnesene was spread on the same kind of sheets of filter paper of the same size.

These two sets of test paper were respectively tied round each seedling of cucumber placed in the field. On the 5th day, the number of alate aphids on each seedling of cucumber were counted.

There were remarkably fewer alate aphids on the seedlings which were rounded with the test paper containing microencapsulated pheromone, comparing that of neat pheromone.

TABLE 2

| Chemical applied into soil in seedling box | Chemical applied on soil in seedling box before 5 hours of transplantation | Growth of the seedlings (%)* | | | | Disease Control (%) against *Pyricularia oryzae* |
|---|---|---|---|---|---|---|
| | | Height (aerial) | Length of root | Weight (a)* | Weight (b)* | |
| Microencapsulated probenazole, Example 5 | none | 95 | 94 | 96 | 98 | 87.9 |
| Microencapsulated probenazole, Example 6 | none | 101 | 102 | 102 | 103 | 90.1 |
| Commercialized granular formulation of probenazole | none | 61 | 56 | 68 | 71 | could not be transplanted |
| None (Control) | Commercialized granular formulation of probenazole | 100 | 100 | 100 | 100 | 88.3 |

Notes:
Taking data of control as 100
(a) weight of raw plant, and
(b) weight of dried plant.

EXAMPLE 17

A test of weed control was carried out in an actual field by after application of the microencapsulated ethyl N,N-di-n-propyl thiocarbamate (so-called EPTC in Japan) prepared in Example 7 as compared to the effect of after application of a commercialized granular formulation containing 5% by weight of ethyl N,N-di-n-propyl thiocarbamate as follows:

After planting seed potatoes in an upland field following the conventional operation, the microencapsulated agricultural chemical prepared in Example 7 containing 86% by weight of ethyl N,N-di-n-propyl thiocarbamate and the commercial granular formulation containing 5% by weight of the same chemical were respectively applied onto the surface of soil of the field where the

EXAMPLE 19

The microencapsulated butachlor prepared in Example 8 was spread on the surface of a paddy field in the amount corresponding to 15 g of the active ingredient per one are and water was put on the paddy field with the depth of 3 cm. Seeds of Barnyardgrass were sown on each area divided into five areas of the paddy field on the 7th day, 14th day, 21st day, 28th day and 35th day, respectively, after the microcapsules were spread. On the 14th day after sowing the seeds, the germinating level of Barnyardgrass was observed to estimate the herbicidal activity of butachlor.

For comparison, commercial granules of 5% butachlor were examined by the same method as above.

The results are shown in Table 3.

The herbicidal activity was calculated by the following formula.

$$\text{Herbicidal activity (\%)} = \frac{C - T}{C} \times 100$$

wherein C is the number of weeds germinated in a control area untreated with any chemical substance and T is the number of weeds germinated in the area spread by the microencapsulated butachlor.

TABLE 3

| Days of sowing seeds after treating with chemical | Herbicidal activity (%) | |
| --- | --- | --- |
|  | Microencapsulated butachlor | Commercial granules of 5% butachlor |
| 7 | 100 | 100 |
| 14 | 100 | 100 |
| 21 | 100 | 90 |
| 28 | 100 | 90 |
| 35 | 100 | 70 |

What is claimed is:

1. A process for preparing a microencapsulated agricultural chemical, comprising
    dispersing an agricultural chemical having a solubility of not more than 1 g in 100 ml of water at 20° C. and a vapor pressure of not more than 760 mmHg at 60° C. in an aqueous medium consisting essentially of a water-soluble cationic urea resin, an anionic surfactant selected from the group consisting of salts of aliphatic acids, sulfate esters of higher alcohols, and salts of alkylaryl sulfonic acids and at least one prepolymer formed from formaldehyde and at least one compound selected from the group consisting of urea, melamine, and thiourea, and
    maintaining the pH of the obtained dispersion within an acidic range to polycondense the water-soluble cationic urea resin and said prepolymer by adding an acid catalyst.
2. The process of claim 1, wherein the prepolymer is a urea-formaldehyde prepolymer.
3. The process of claim 1, wherein the prepolymer is a melamine-formaldehyde prepolymer.
4. The process of claim 1, wherein the prepolymer is a urea-melamine-formaldehyde prepolymer.
5. The process of claim 1, wherein the prepolymer is a thio-urea-melamine-formaldehyde prepolymer.
6. The process of any one of claims 2 and 1, wherein the agricultural chemical is a pesticide.
7. The process of any one of claims 2 and 1, wherein the agricultural chemical is a fungicide.
8. The process of any one of claims 2 and 1, wherein the agricultural chemical is pheromone.
9. The process of claim 1, wherein the dispersion is maintained at pH of 2.5 to 6.0 and the temperature of 15° to 60° C. for 2 to 50 hours.
10. A microencapsulated agricultural chemical produced by the process of claim 1.

* * * * *